United States Patent
Sang et al.

(10) Patent No.: US 10,995,572 B2
(45) Date of Patent: May 4, 2021

(54) SIMULATION TEST METHOD FOR GAS EXTRACTION FROM TECTONICALLY-DEFORMED COAL SEAM IN-SITU BY DEPRESSURIZING HORIZONTAL WELL CAVITY

(71) Applicants: China University of Mining and Technology, Jiangsu (CN); XUZHOU OLIVINE GEOSCIENCE & GEOTECH CO., LTD, Jiangsu (CN); CHINA UNIVERSITY OF PETROLEUM, EAST CHINA, Shandong (CN); ANHUI UNIVERSITY OF SCIENCE AND TECHNOLOGY, Anhui (CN); WUHAN INSTITUTE OF TECHNOLOGY, Hubei (CN)

(72) Inventors: Shuxun Sang, Jiangsu (CN); Xiaozhi Zhou, Jiangsu (CN); Liweng Cao, Jiangsu (CN); Shiqi Liu, Jiangsu (CN); Haiwen Wang, Shandong (CN); Huihu Liu, Anhui (CN); Zicheng Li, Hubei (CN); Jinlong Jia, Hubei (CN); Huazhou Huang, Jiangsu (CN); Changjiang Liu, Shandong (CN); Hongjie Xu, Anhui (CN); Ran Wang, Jiangsu (CN); Shuyun Zhu, Jiangsu (CN)

(73) Assignees: China University of Mining and Technology, Jiangsu (CN); XUZHOU OLIVINE GEOSCIENCE & GEOTECH CO., LTD, Jiangsu (CN); CHINA UNIVERSITY OF PETROLEUM, EAST CHINA, Shandong (CN); ANHUI UNIVERSITY OF SCIENCE AND TECHNOLOGY, Anhui (CN); WUHAN INSTITUTE OF TECHNOLOGY, Hubei (CN)

( * ) Notice: Subject to any disclaimer, the term of this patent is extended or adjusted under 35 U.S.C. 154(b) by 0 days.

(21) Appl. No.: 16/761,497
(22) PCT Filed: Nov. 12, 2018
(86) PCT No.: PCT/CN2018/114946
§ 371 (c)(1),
(2) Date: May 4, 2020

(87) PCT Pub. No.: WO2019/205577
PCT Pub. Date: Oct. 31, 2019

(65) Prior Publication Data
US 2020/0263511 A1    Aug. 20, 2020

(30) Foreign Application Priority Data
Apr. 28, 2018    (CN) .......................... 201810404471.7

(51) Int. Cl.
*E21B 21/06*    (2006.01)
*E21B 7/04*    (2006.01)
(Continued)

(52) U.S. Cl.
CPC ............ *E21B 21/063* (2013.01); *E21B 7/046* (2013.01); *E21B 7/18* (2013.01); *E21B 7/28* (2013.01);
(Continued)

(58) Field of Classification Search
CPC ........ E21C 41/18; E21B 21/063; E21B 7/046; E21B 7/18; E21B 7/28; E21B 43/12;
(Continued)

(56) References Cited

U.S. PATENT DOCUMENTS
2007/0062693 A1    3/2007    Chan et al.

FOREIGN PATENT DOCUMENTS
CN    201037402        3/2008
CN    102536302 A *    7/2012
(Continued)

OTHER PUBLICATIONS
"International Search Report (Form PCT/ISA/210) of PCT/CN2018/114946," dated Feb. 3, 2019, with English translation thereof, pp. 1-4.

*Primary Examiner* — Kristyn A Hall
*Assistant Examiner* — Dany E Akakpo
(74) *Attorney, Agent, or Firm* — JCIPRNET

(57) ABSTRACT

A simulation test method for gas extraction from a tectonically-deformed coal seam in-situ by depressurizing a horizontal well cavity. A coal series stratum structure reconstruction and similar material simulation subsystem simulates a tectonically-deformed coal reservoir. A horizontal well drilling and reaming simulation subsystem con-
(Continued)

structs a U-shaped well in which a horizontal well adjoins a vertical well, and performs a reaming process on a horizontal section thereof. A horizontal well hole-collapse cavity-construction depressurization excitation simulation subsystem performs pressure-pulse excitation and stress release on the horizontal well, and hydraulically displaces a coal-liquid-gas mixture such that the mixture is conveyed towards a vertical well section. A product lifting simulation subsystem further pulverizes the coal and lifts the mixture. A gas-liquid-solid separation simulation subsystem separates the coal, liquid and gas. A monitoring and control subsystem detects and controls the operation and the execution processes of equipment in real time.

5 Claims, 4 Drawing Sheets

(51) Int. Cl.
| | | |
|---|---|---|
| E21B 7/18 | (2006.01) | |
| E21B 7/28 | (2006.01) | |
| E21B 43/12 | (2006.01) | |
| E21C 41/18 | (2006.01) | |
| G06F 11/34 | (2006.01) | |
| G01N 33/24 | (2006.01) | |

(52) U.S. Cl.
CPC .............. *E21B 43/12* (2013.01); *E21C 41/18* (2013.01); *G01N 33/24* (2013.01); *G06F 11/3457* (2013.01); *G06F 11/3466* (2013.01); *G01N 2203/003* (2013.01); *G01N 2203/0058* (2013.01); *G01N 2203/0208* (2013.01); *G01N 2203/0256* (2013.01)

(58) Field of Classification Search
CPC .............. G01N 33/24; G01N 2203/003; G01N 2203/0058; G01N 2203/0208; G01N 2203/0256; G06F 11/3457; G06F 11/3466
See application file for complete search history.

(56) References Cited

FOREIGN PATENT DOCUMENTS

| CN | 103114827 | | 5/2013 |
|---|---|---|---|
| CN | 103114870 | | 5/2013 |
| CN | 105064920 | | 11/2015 |
| CN | 107762451 A | * | 3/2018 |
| WO | 2016076537 | | 5/2016 |

* cited by examiner

SIMULATION TEST METHOD FOR GAS EXTRACTION FROM TECTONICALLY-DEFORMED COAL SEAM IN-SITU BY DEPRESSURIZING HORIZONTAL WELL CAVITY

CROSS-REFERENCE TO RELATED APPLICATION

This application is a 371 of international application of PCT application serial no. PCT/CN2018/114946, filed on Nov. 12, 2018, which claims the priority benefit of China application no. 201810404471.7, filed on Apr. 28, 2018. The entirety of each of the above mentioned patent applications is hereby incorporated by reference herein and made a part of this specification.

FIELD OF THE INVENTION

The present invention relates to the field of coal seam gas extraction, and relates to a simulation test method for coal seam gas extraction, and in particular, to a simulation test method for gas extraction from a tectonically-deformed coal seam in-situ by depressurizing a horizontal well cavity.

DESCRIPTION OF RELATED ART

Tectonically-deformed coal refers to coal whose coal seam is subject to tectonic stress and whose primary structure and construction are significantly destroyed due to cracking, resulting in fractures, wrinkles, polished surfaces, and other structural changes. The extensive development of tectonically-deformed coal and the richness of tectonically-deformed coal seam gas resources are distinguishing features of coal and coal seam gas resources in China. Tectonically-deformed coal resources account for a very high proportion of coal resources that have been discovered in China, and a proportion of a quantity of tectonically-deformed coal seam gas resources to a total quantity of coal seam gas resources in China is larger. Tectonically-deformed coal has prominent features such as rich gas, low permeability, and looseness, and most of tectonically-deformed coal are coal and gas outburst coal seams. Due to its hazards and difficulty in extraction and utilization, the tectonically-deformed coal is mostly discharged into the atmosphere in coal production. The efficient development of tectonically-deformed coal seam gas is of great significance for energy, safety and ecology.

A method based on the theory of hydrophobic depressurization, desorption, and gas recovery is a main method for the development of surface wells for in-situ coal seam gas at present. Due to the extremely low permeability of tectonically-deformed coal reservoirs and the poor effect of a reconstruction method such as hydraulic fracturing, the theory of hydrophobic depressurization, desorption, and gas recovery is not suitable for tectonically-deformed coal reservoirs. The results of exploration and development practice also show that all coal seam gas exploration and development technologies based on the theory of hydrophobic depressurization, desorption, and gas recovery, including SVR technologies (vertical well fracturing, U-shaped well fracturing, multi-branched horizontal well fracturing, horizontal well fracturing, and the like), ECBM technologies ($CO_2$-ECBM, $N_2$-ECBM, and the like) and their combined technologies, fail to achieve efficient development of tectonically-deformed coal seam gas. Therefore, efficient exploration and development technologies and equipment for tectonically-deformed coal seam gas have become one of important technical bottlenecks restricting the rapid and scale development of the China's coal seam gas industry.

With the in-depth study of coal seam gas extraction technologies, the development theory of mining-induced pressure relief and permeability improvement for tectonically-deformed coal seam gas in a protected layer in a coal mine area provides a new idea for in-situ extraction of tectonically-deformed coal seam gas. However, in actual extraction application, due to the characteristics of tectonically-deformed coal, there are problems such as wellbore fractures caused by overburden deformation and difficulty in connecting coal to coal seam gas production. Therefore, the research and development of a technical theory and a simulation test method that are suitable for in-situ extraction of tectonically-deformed coal seam gas is an important theoretical and practical way to break the technical bottleneck of efficient development of surface wells for tectonically-deformed coal seam gas in China and realize the exploration and development of coal seam gas in China.

SUMMARY OF THE INVENTION

To resolve the foregoing problem, the present invention provides a simulation test method for gas extraction from a tectonically-deformed coal seam in-situ by depressurizing a horizontal well cavity, which enables the simulation of an extraction process including completion of a large-diameter horizontal well in a loose tectonically-deformed coal reservoir, horizontal well cavity-construction stress release, effective lifting of mixed fluids, and efficient separation of produced mixtures, thereby providing guidance for efficient and continuous in-situ extraction of tectonically-deformed coal seam gas.

To achieve the foregoing objective, the present invention adopts the following technical solution: a simulation test method for gas extraction from a tectonically-deformed coal seam in-situ by depressurizing a horizontal well cavity. A coal series stratum structure reconstruction and similar material simulation subsystem 1 simulates an actual tectonically-deformed coal reservoir. A horizontal well drilling and reaming simulation subsystem constructs a U-shaped well in which a horizontal well adjoins a vertical well, and performs a reaming process on a horizontal section of the horizontal well. A horizontal well hole-collapse cavity-construction depressurization excitation simulation subsystem performs pressure-pulse excitation and stress release on the horizontal well, and hydraulically displaces a coal-liquid-gas mixture such that the mixture is conveyed towards a vertical well section along a depressurizing space. A product lifting simulation subsystem further pulverizes the coal and lifts the produced mixture to a wellhead of the vertical well. A gas-liquid-solid separation simulation subsystem separates the coal, liquid and gas. A monitoring and control subsystem detects and controls the operation and the execution processes of test equipment in real time, so as to collect, display, process, and analyze test data. Specific steps are as follows:

1) According to actual geological characteristics of the tectonically-deformed coal reservoir and based on a similarity principle, configuring similar simulation materials with corresponding physical and mechanical characteristics, disposing the similar simulation materials in a triaxial stress-tight stereo support, and arranging a stress sensor, a temperature sensor, and a strain gauge.

Preheating the triaxial stress-tight stereo support in a constant temperature room to reach a test design temperature.

Starting an air compressor and a gas booster pump, injecting gas into a similar material coal seam, starting an X-direction servo loading system, a Y-direction servo loading system, and a Z-direction servo loading system, increasing a three-way confining pressure to a test design pressure for the triaxial stress-tight stereo support, checking the airtightness of the device; and if the airtightness meets a requirement, performing a next step; or if the airtightness does not meet a requirement, repeating this step.

2) Arranging various devices and connecting the corresponding devices, and using an existing drilling tool and processing technology to construct vertical well sections and kick-off sections of the vertical well and the horizontal well to the similar material coal seam.

3) Replacing the drilling tool with a reciprocating drilling and reaming tool and lowering the reciprocating drilling and reaming tool to the kick-off section of the horizontal well, performing three-stage reaming and large-diameter well completion on the similar material coal seam, and forming a horizontal well section that runs through the vertical well, to achieve open-hole cavity-constructing completion.

4) Removing all drilling tools from the well, and lowering an underground injection device and a copper strip connected to a high level end of a power supply to a starting point of the horizontal section of the horizontal well, lowering gas-liquid-coal mixture lifting and production devices, namely, a pulverization disturbance device and a hydraulic jet pump to the vertical well, and connecting the wellhead of the vertical well to a coal-liquid-gas separation device.

5) Starting a plunger pump, injecting high-pressure high-speed fluids into the horizontal section of the horizontal well at a specified frequency, to cut and pulverize a coal rock and form a depressurization cavity, then accelerating water into high-velocity jet flows, to further pulverize and flush coal powder, and conveying a formed gas-liquid-coal mixture to the bottom of the vertical well.

6) Starting the underground pulverization disturbance device and hydraulic jet pump, further pulverizing the coal powder that flows into the bottom of the vertical well, and then lifting the coal powder to the ground to enter the coal-liquid-gas separation device.

7) Separating the mixture that enters the coal-liquid-gas separation device, and allowing coal seam gas, an excitation liquid, and coal powder that are separated to respectively enter a gas collection bottle, a wastewater collection and treatment device, and a coal powder storage device.

8) Starting a return water pump and transferring the treated excitation liquid to a water tank for recycling.

The monitoring and control simulation subsystem collects corresponding related data such as a time, pressure, a temperature, stress-strain, saturation, a voltage/current, sedimentation solid mass, produced liquid mass, and a produced gas flow while controlling the foregoing respective steps, and records the data as a data file.

Further, in step 3), three-stage reaming rates are respectively 150%, 200%, and 300%, and a diameter increase after reaming is 200% to 300%.

Further, in step 5), a depressurization excitation range after the pressure-pulse excitation and the stress release are performed on the horizontal well is ≥15 times a coal thickness.

Further, in step 6), coal powder concentration after pulverization is ≤50%.

Further, in step 5), the high-pressure high-speed fluids are mixed with a particular proportion of an abrasive.

In the present invention, based on the similarity principle, the similar simulation materials with the corresponding physical and mechanical characteristics are configured for the tectonically-deformed coal reservoir; high-pressure gas is injected into the similar material coal seam by means of a high-pressure gas cylinder to simulate geological pressure inside the coal seam; and coal seam confining pressure is simulated through three-dimensional loading to the triaxial stress-tight stereo support, to provide a basis for real and accurate simulation of in-situ extraction of the tectonically-deformed coal seam gas as much as possible.

In the present invention, the drilling tool in the horizontal well drilling and reaming subsystem is designed into a three-stage drilling and reaming tool; and further reaming is implemented through two-way reciprocating drilling construction after drilling in the horizontal section of the horizontal well. In this way, the diameter of the horizontal section is greatly increased, the problem of wellbore collapse induced by overburden deformation resulting from the loose tectonically-deformed coal is avoided, and continuous in-situ extraction of tectonically-deformed coal seam gas is ensured.

After the open-hole cavity-constructing completion through reaming of the horizontal well, the high-pressure high-speed fluids are injected into the horizontal well cavity at a particular pulse frequency to further cut and pulverize the medium, to simulate the pressure-pulse excitation and the stress release on the horizontal well of the tectonically-deformed coal seam gas, and hydraulically displace the coal-liquid-gas mixture such that the mixture is conveyed towards the vertical well section along the depressurizing space. In this way, subsequent lifting is ensured.

The coal powder is further pulverized and the mixture is lifted towards the wellhead of the vertical well through cooperation of the underground pulverization disturbance device and hydraulic jet pump; and efficient coal-liquid-gas separation for the produced mixture and recycling of the excitation liquid are achieved through the coal-liquid-gas separation device.

Real-time detection and control of the operation conditions and the execution processes of the test equipment are implemented through three layers of network architecture and software including on-site workstations, monitoring instruments and sensors, and a central server control system, so as to collect, display, process, and analyze the test data. The coordinated operation of subsystems in the entire extraction system achieves simulation of efficient and continuous in-situ extraction of the tectonically-deformed coal seam gas.

DETAILED DESCRIPTION OF THE INVENTION

Figure 1:
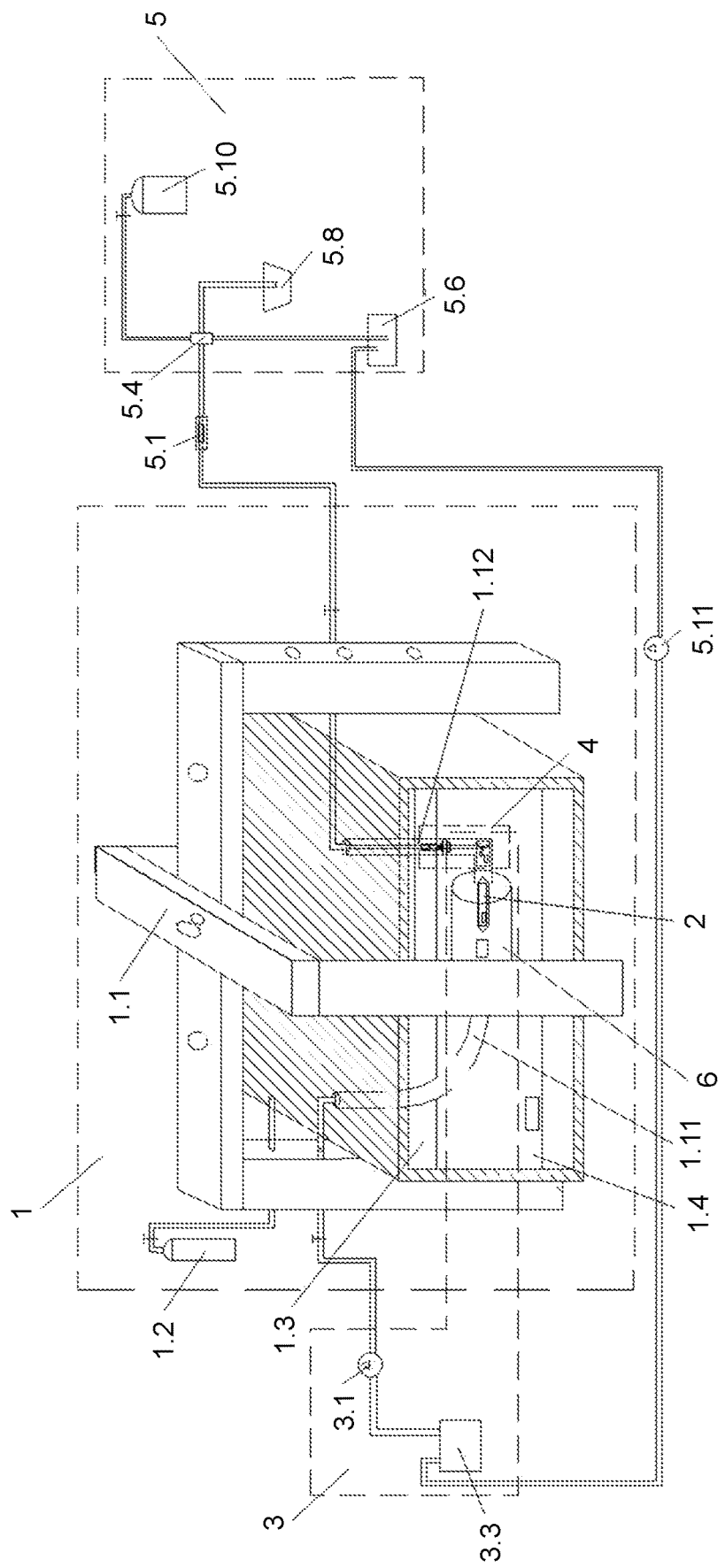
FIG. 1 is an overall principle diagram of a test system used in the present invention.
Figure 2:
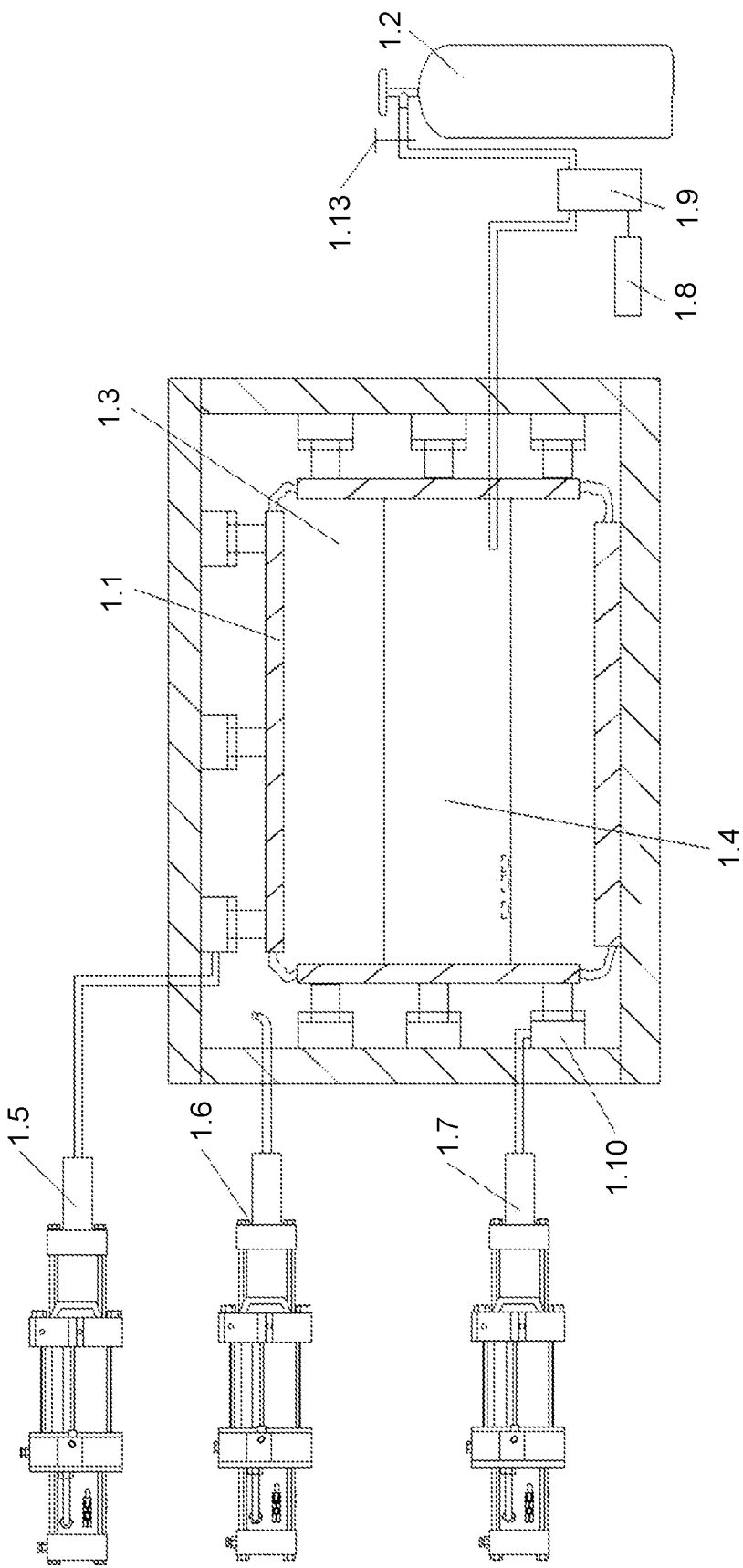
FIG. 2 is a schematic diagram of a coal series stratum structure reconstruction and similar material simulation subsystem in a test system used in the present invention.

The present invention is further described below with reference to the accompanying drawings (a left-right direction in the following description is the same as a left-right direction in FIG. 1).

FIG. 1 to FIG. 4 show a simulation test system used in the present invention, which includes a coal series stratum structure reconstruction and similar material simulation subsystem 1, a horizontal well drilling and reaming simulation subsystem 2, a horizontal well hole-collapse cavity-construction depressurization excitation simulation subsystem 3, a product lifting simulation subsystem 4, a gas-liquid-solid separation simulation subsystem 5, and a monitoring and control subsystem. The coal series stratum structure reconstruction and similar material simulation subsystem 1 includes a triaxial stress-tight stereo support 1.1, a similar material surrounding rock 1.3, a similar material coal seam 1.4, a high-pressure gas cylinder 1.2, and a gas booster pump 1.9. The triaxial stress-tight stereo support 1.1 is formed by connecting sixth movable steel plates to form a sealed hexahedron, in which the similar material surrounding rock 1.3 and the similar material coal seam 1.4 are disposed. Two layers of similar material surrounding rocks 1.3 are respectively located above and below the similar material coal seam 1.4 to simulate a coal seam top plate and a coal seam bottom plate. An X-direction servo loading system 1.7, a Y-direction servo loading system 1.6, and a Z-direction servo loading system 1.5 are respectively in a hydraulic connection with a corresponding load piston 1.10 outside the triaxial stress-tight stereo support 1.1, and are configured to increase confining pressure for the similar material coal seam 1.4. An inlet of the gas booster pump 1.9 is in communication with an outlet of the high-pressure gas cylinder 1.2, an outlet pipeline of the gas booster pump 1.9 is disposed in the similar material coal seam 1.4, and a power input port is in communication with an outlet of an air compressor 1.8, and is configured to increase gas pressure in a coal seam for the similar material coal seam 1.4. A sixth valve 1.13 is disposed at an outlet of the high-pressure gas cylinder 1.2, and is configured to control gas release in the high-pressure gas cylinder 1.2. A pressure sensor (not shown), a temperature sensor (not shown), and a strain gauge (not shown) are disposed in the similar material coal seam 1.4 near a lower end, and are configured to measure pressure, a temperature, and strain in the similar material coal seam 1.4 during a test.

The horizontal well drilling and reaming simulation subsystem includes a simulation drilling rig (not shown), a drill column string (not shown), a drilling tool, and a drilling fluid circulation system. A connection between the simulation drilling rig and the drill column string is the same as that in the prior art. The simulation drilling rig is configured to power the drilling tool. The drill column string is a string consisting of a Kelly bar, a drill pipe, a drill collar, and another underground tool, and is configured to install the drilling tool. The drilling tool is a reciprocating drilling and reaming tool. The drilling tool, from a connection end with the drill column string to a drilling end, includes a third-stage reaming and retraction assembly 2.3, a primary and secondary reaming and retraction assembly 2.2, and a pilot assembly 2.1 respectively. The third-stage reaming and retraction assembly 2.3 includes a plurality of expandable and closable blades 2.5 that is circumferentially disposed. The blade 2.5 is locked and positioned by a second locking mechanism 2.6. The primary and secondary reaming and retraction assembly 2.2 includes a plurality of extendable and retractable plunger drill bits 2.4 that is circumferentially disposed. The plunger drill bit 2.4 is locked and positioned by a first locking mechanism 2.7. A connection between a drilling fluid positive circulation system and another component is the same as that in the prior art. The drilling tool is provided with a drill bit positioning sensor and a drilling speed sensor, and is configured to monitor a drill bit position and a drilling speed. During drilling construction of a horizontal well 1.11, during running towards the direction of a vertical well 1.12, the plunger drill bit 2.4 is extended to start drilling, and during returning towards the direction of the simulation drilling rig, the blade 10.5 is opened. Because the diameter after the blade 10.5 is opened is greater than the diameter when the plunger drill bit 10.4 is extended, the horizontal well is reamed, thereby achieving three-stage reaming in rock mass at drillability classes I, II, III, IV and V. Three-stage reaming rates respectively reach 150%, 200%, 300%, and a diameter increase after reaming is 200% to 300%.

The horizontal well hole-collapse cavity-construction depressurization excitation simulation subsystem includes a plunger pump 3.1, a water tank 3.3, a power supply 3.10, a measurement device 3.11, and an underground injection device 3.12. An inlet of the plunger pump 3.1 is in communication with the water tank 3.3, and an outlet of the plunger pump 3.1 is in communication with the underground injection device 3.12. The underground injection device 3.12 is disposed at one side of a horizontal section of the horizontal well 1.11 near a wellhead. A high level end of the power supply 3.10 is connected to a copper strip disposed in the horizontal well 1.11, and a low level end of the power supply 3.10 is connected to a high level end of the measurement device 3.11. A low level end of the measurement device 3.11 is electrically connected to a copper strip on an outer surface of the triaxial stress-tight stereo support 1.1. An underground pressure sensor and a saturation probe are disposed in the horizontal well 1.11 near the vertical well 1.12. A first valve 3.9 and a first pressure sensor 3.8 are disposed at a liquid inlet pipeline at the wellhead of the horizontal well 1.11, and are configured to control injection of an excitation liquid into the horizontal well 1.11 and monitor injection pressure. After the open-hole cavity-constructing completion through reaming of the horizontal well 1.11, the plunger pump 3.1 injects high-pressure high-speed fluids to a horizontal well cavity at a particular pulse frequency, which are sprayed by the underground injection device 3.12 to the horizontal section of the horizontal well 1.11 to form a depressurization cavity 6, to implement pressure-pulse excitation and stress release on the horizontal well of tectonically-deformed coal seam gas; and a gas-liquid-coal mixture is displaced through the injected high-pressure high-speed fluids such that the mixture is conveyed towards the vertical well 1.12 along a depressurizing space and then produced. A depressurization excitation range (a stress release area width/a coal thickness) after the pressure-pulse excitation and the stress release are performed on the horizontal well is ≥15. During depressurization excitation, the measurement device 3.11 monitors an underground voltage field and current field, and the underground pressure sensor and the saturation probe measure underground pressure and saturation.

The product lifting simulation subsystem includes a pulverization disturbance device 4.1 and a hydraulic jet pump 4.2. The hydraulic jet pump 4.2 is a wide-flow jet pump, is disposed in the vertical well 1.12 near the bottom of the well, and is configured to lift the gas-liquid-coal mixture to the wellhead. The pulverization disturbance device 4.1 is disposed at the bottom of the vertical well 1.12 and at a joint between the depressurization cavity 6 and the vertical well 1.12 for pulverizing coal powder at the bottom of the well, so that the coal powder can be more easily lifted by the hydraulic jet pump 4.2 to the wellhead of the vertical well 1.12. In this way, fluids with coal powder concentration≤50% are efficiently produced.

The gas-liquid-solid separation simulation subsystem includes a coal-liquid-gas separation device 5.4, a wastewater collection and treatment device 5.6, a coal powder storage device 5.8, and a gas collection bottle 5.10. An inlet of the coal-liquid-gas separation device 5.4 is in communication with a wellhead pipeline of the vertical well 1.12, and three outlets of the coal-liquid-gas separation device 5.4 are in communication with the wastewater collection and treatment device 5.6, the coal powder storage device 5.8, and the gas collection bottle 5.10 respectively. A second valve 5.2, a coal-water-gas component sensor 5.1, and a second pressure sensor 5.3 are disposed on the wellhead pipeline of the vertical well 1.12, and are configured to control discharge of the product in the vertical well, and detect components and pressure of the discharged product respectively. The subsystem can achieve gas-liquid-coal mixture pre-treating, gas separation, liquid-coal separation, coal-gas collection, excitation liquid (or water) purification and recycling, with gas separation efficiency of above 90% to 95%, excitation liquid separation and collection efficiency of above 80% to 90%, and a coal powder collection capability of above 98%.

The monitoring and control subsystem includes three layers of network architecture and software including on-site workstations, monitoring instruments and sensors, and a central server control system. Based on a high-precision sensor technology, through construction of the three layers of network architecture including the sensors, the on-site workstations, and the central server control system, and application of a database technology and a filtering algorithm, real-time storage and high-precision processing of mass data are implemented; an intelligent algorithm is used to implement closed loop control of physical parameters of a test platform; and configuration analysis software and an Internet of Things perception technology are applied, to form a data acquisition and monitoring system that is "accurate, visual, interactive, fast, and intelligent" to detect and control the operation conditions and the execution processes of the test system in real time, so as to collect, display, process, and analyze engineering data.

Figure 4:
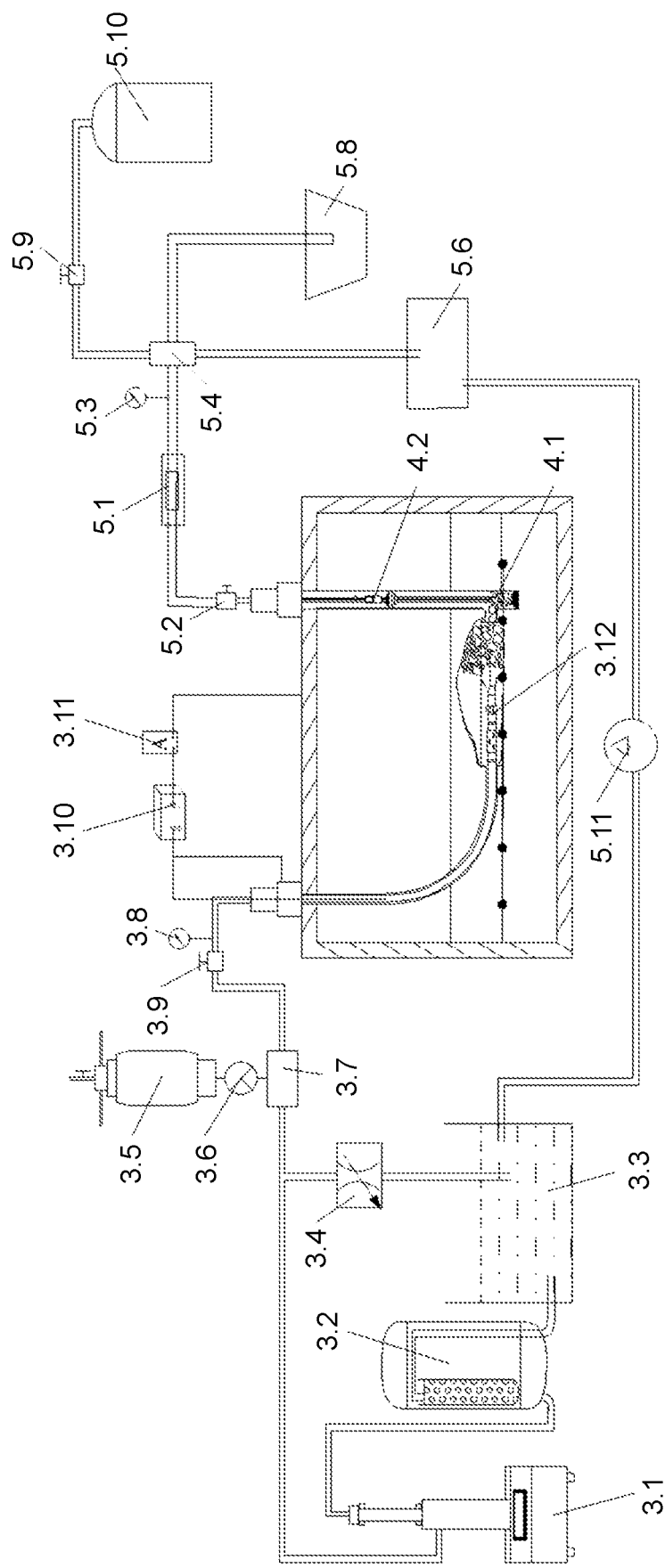
FIG. 4 is a schematic diagram of a depressurization excitation simulation subsystem, a product lifting simulation subsystem, and a gas-liquid-solid separation simulation subsystem in a test system used in the present invention.

As shown in FIG. 1 and FIG. 4, the horizontal well hole-collapse cavity-construction depressurization excitation simulation subsystem further includes an abrasive tank 3.5 and a mixing chamber 3.7. An outlet of the abrasive tank 3.5 is in communication with an outlet of the plunger pump 3.1 and the mixing chamber 3.7. An outlet of the mixing chamber 3.7 is in communication with the underground injection device 3.12. The addition of a particular proportion of an abrasive to the excitation liquid improves the capability of the excitation liquid to cut a coal rock, thereby improving extraction efficiency. A stop valve 3.5 is disposed at the outlet of the abrasive tank 3.5, and is configured to control abrasive input to the mixing chamber 3.7. A branch in communication with the water tank 3.3 is disposed on an outlet pipeline of the plunger pump 3.1, and a pressure regulating valve 3.4 is disposed on the branch, and is configured to control pressure of the excitation liquid.

Figure 3A:
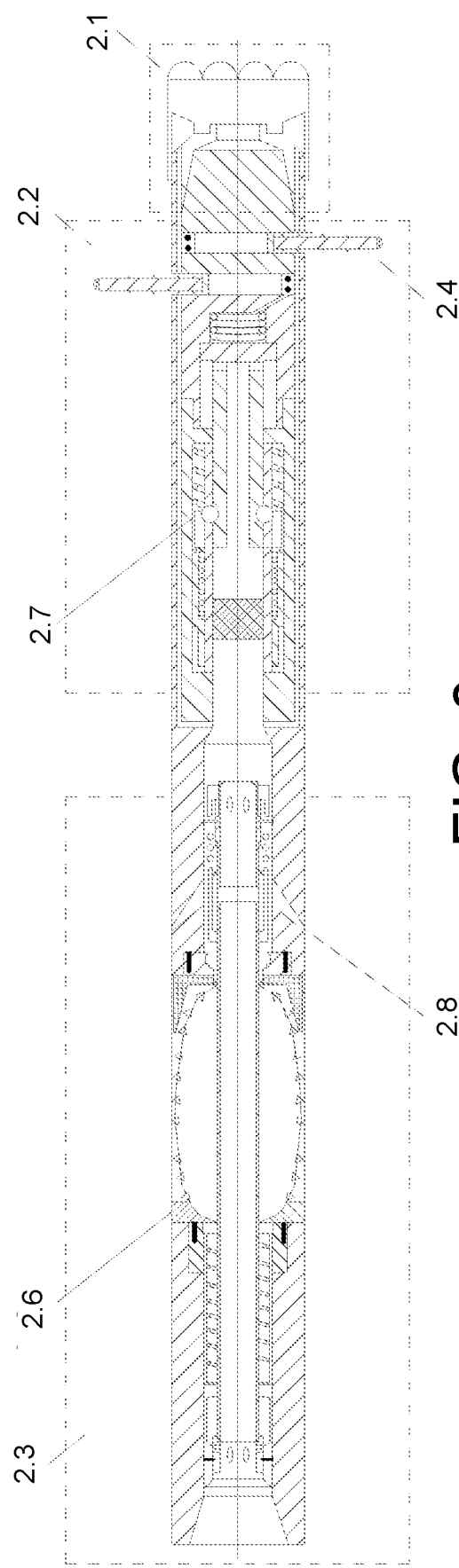
FIG. 3a is a schematic state diagram of drilling of the drilling tool.
Figure 3B:
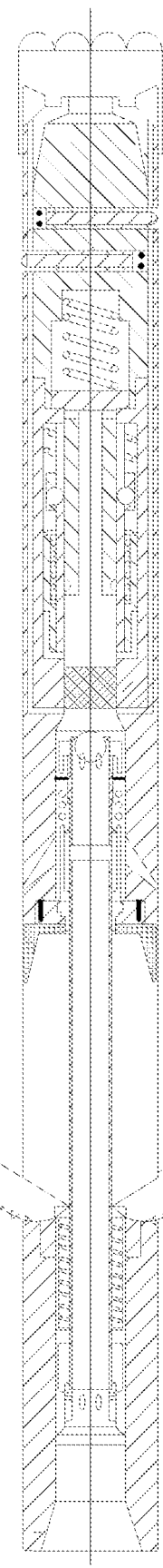
FIG. 3b is a schematic state diagram of reaming of the drilling tool.

As shown in FIG. 1, FIG. 3a, and FIG. 3b, the blade 2.5 on the drilling tool is rotated and opened towards the direction of the wellhead of the horizontal well. A drilling fluid outlet 2.8 is disposed on the right of the blade 2.5, and gradually inclines towards the direction of the blade 2.5 when extending towards the outer circumference of the drilling tool from an inner cavity of the drilling tool. During drilling, drilling fluids can achieve cooling and auxiliary cutting functions like conventional drilling fluids, and can also provide sufficient support for the expansion of the blade 2.5, to reduce rigid deformation of a connecting member with the blade 2.5, and prolong a service life of the device.

As shown in FIG. 1 and FIG. 4, the simulation test system further includes a return water pump 5.11. An inlet of the return water pump 5.11 is in communication with the wastewater collection and treatment device 5.6, and an outlet of the return water pump 5.11 is in communication with the water tank 3.3. Separated excitation liquid is treated and then enters the water tank 3.3 for recycling, thereby ensuring continuity of the test and saving resources.

A filter 3.2 is connected between the plunger pump 3.1 and the water tank 3.3, and is configured to filter out impurities in water that flows from the water tank 3.3 into the plunger pump 3.1, to prevent impurities in recycling water from damaging the plunger pump 3.1.

The strain gauge is preferably a distributed optical fiber measurement instrument that can be longitudinally distributed along the similar material coal seam 1.4, so that measured strain data is more accurate.

A simulation test method for gas extraction from a tectonically-deformed coal seam in-situ by depressurizing a horizontal well cavity includes the following steps.

According to actual geological characteristics of a tectonically-deformed coal reservoir and based on a similarity principle, configuring similar simulation materials with corresponding physical and mechanical characteristics, disposing the similar simulation materials in a triaxial stress-tight stereo support 1.1, and arranging a stress sensor, a temperature sensor, and a strain gauge.

Preheating the triaxial stress-tight stereo support 1.1 in a constant temperature room to reach a test design temperature.

Opening a sixth valve 1.13, starting an air compressor 1.8 and a gas booster pump 1.9, injecting gas into a similar material coal seam 1.4, starting an X-direction servo loading system, a Y-direction servo loading system, and a Z-direction servo loading system, increasing a confining pressure to a test design pressure for the triaxial stress-tight stereo support 1.1, checking the airtightness of the device; and if the airtightness meets a requirement, performing a next step; or if the airtightness does not meet a requirement, repeating this step.

2) Arranging various devices and connecting the corresponding devices, and using an existing drilling tool and processing technology to construct vertical well sections and kick-off sections of a vertical well 1.12 and a horizontal well 1.11 to the similar material coal seam 1.4, where a drilling fluid circulation system provides drilling fluids for the underground during construction.

3) Replacing the drilling tool with a reciprocating drilling and reaming tool and lowering the reciprocating drilling and reaming tool to the kick-off section of the horizontal well, performing three-stage reaming and large-diameter well completion on the similar material coal seam 1.4, and forming a horizontal well section that runs through the vertical well 1.12 (forming a U-shaped well in which the horizontal well adjoins the vertical well), to achieve open-hole cavity-constructing completion, where the drilling fluid circulation system provides the drilling fluids for the underground during construction.

4) Removing all drilling tools from the well, and lowering an underground injection device 3.12 and a copper strip connected to a high level end of a power supply 3.10 to a starting point of the horizontal section of the horizontal well 1.11, lowering gas-liquid-coal mixture lifting and production devices, namely, a pulverization disturbance device 4.1 and a hydraulic jet pump 4.2 to the vertical well 1.12, and connecting a wellhead of the vertical well 1.12 to a coal-liquid-gas separation device 5.4.

5) Opening a first valve 3.9, starting a plunger pump 3.1, injecting high-pressure high-speed fluids into the horizontal section of the horizontal well 1.11 at a specified frequency, to cut and pulverize a coal rock and implement pressure-pulse excitation and stress release on the horizontal section of the horizontal well 1.11 to form a depressurization cavity 6, then accelerating water into high-velocity jet flows, to further pulverize and flush coal powder, and conveying a formed gas-liquid-coal mixture to the bottom of the vertical well 1.12, where during the pressure-pulse excitation and the stress release on the horizontal section of the horizontal well 1.11, a particular proportion of an abrasive may be mixed in the excitation liquid to improve the capability of the excitation liquid to cut a coal rock, thereby improving extraction efficiency.

6) Opening a second valve 5.2 and a fifth valve 5.9, starting the underground pulverization disturbance device 4.1 and hydraulic jet pump 4.2, further pulverizing the coal powder that flows into the bottom of the vertical well 1.12, and then lifting the coal powder to the ground to enter the coal-liquid-gas separation device 5.4.

7) Separating the mixture that enters the coal-liquid-gas separation device 5.4, and allowing coal seam gas, an excitation liquid, and coal powder that are separated to respectively enter a gas collection bottle 5.10, a wastewater collection and treatment device 5.6, and a coal powder storage device.

8) Starting a return water pump 5.11 and transferring the treated excitation liquid to a water tank 3.3 for recycling.

The monitoring and control simulation subsystem collects corresponding related data such as a time, pressure, a temperature, stress-strain, saturation, a voltage/current, sedimentation solid mass, produced liquid mass, and a produced gas flow while controlling the foregoing respective steps, and records the data as a data file.

What is claimed is:

1. A simulation test method for gas extraction from a tectonically-deformed coal seam in-situ by depressurizing a horizontal well cavity, wherein a coal series stratum structure reconstruction and similar material simulation subsystem simulates an actual tectonically-deformed coal reservoir; a horizontal well drilling and reaming simulation subsystem constructs a U-shaped well in which a horizontal well adjoins a vertical well, and performs a reaming process on a horizontal section of the horizontal well; a horizontal well hole-collapse cavity-construction depressurization excitation simulation subsystem performs pressure-pulse excitation and stress release on the horizontal well, and hydraulically displaces a coal-liquid-gas mixture such that the mixture is conveyed towards the vertical well along a depressurizing space; a product lifting simulation subsystem further pulverizes the coal and lifts the mixture to a wellhead of the vertical well; a gas-liquid-solid separation simulation subsystem separates the coal, liquid and gas; and a monitoring and control subsystem detects and controls operation and execution processes of test equipment in real time, so as to collect, display, process, and analyze test data, wherein specific steps are as follows:

1) according to actual geological characteristics of the tectonically-deformed coal reservoir and based on a similarity principle, configuring similar simulation materials with corresponding physical and mechanical characteristics, disposing the similar simulation materials in a triaxial stress-tight stereo support, and arranging a stress sensor, a temperature sensor, and a strain gauge;

preheating the triaxial stress-tight stereo support in a constant temperature room to reach a test design temperature; and starting an air compressor and a gas booster pump, injecting gas into a similar material coal seam, starting an X-direction servo loading system, a Y-direction servo loading system, and a Z-direction servo loading system, increasing a three-way confining pressure to a test design pressure for the triaxial stress-tight stereo support, checking airtightness of the triaxial stress-tight stereo support; and if the airtightness meets a requirement, performing a next step; or if the airtightness does not meet a requirement, repeating step 1);

2) arranging various devices, and using an existing drilling tool and processing technology to construct a vertical well section and kick-off sections of the vertical well and the horizontal well to the similar material coal seam;

3) replacing the drilling tool with a reciprocating drilling and reaming tool and lowering the reciprocating drilling and reaming tool to a kick-off section of the horizontal well, performing three-stage reaming and large-diameter well completion on the similar material coal seam, and forming a horizontal well section that runs through the vertical well, to achieve open-hole cavity-constructing completion;

4) removing the reciprocating drilling and reaming tool from the horizontal well, and lowering an underground injection device and a copper strip connected to a high level end of a power supply to a starting point of the horizontal section of the horizontal well, lowering gas-liquid-coal mixture lifting and production devices, namely, a pulverization disturbance device and a hydraulic jet pump to the vertical well, and connecting the wellhead of the vertical well to a coal-liquid-gas separation device;

5) starting a plunger pump, injecting high-pressure high-speed fluids into the horizontal section of the horizontal well at a specified frequency, to cut and pulverize a coal rock and form a depressurization cavity, then accelerating water into high-velocity jet flows, to further pulverize and flush coal powder, and conveying a formed gas-liquid-coal mixture to a bottom of the vertical well;

6) starting the underground pulverization disturbance device and the hydraulic jet pump, further pulverizing the coal powder that flows into the bottom of the vertical well, and then lifting the coal powder to the ground to enter the coal-liquid-gas separation device;

7) separating the mixture that enters the coal-liquid-gas separation device, and allowing coal seam gas, an excitation liquid, and coal powder that are separated to respectively enter a gas collection bottle, a wastewater collection and treatment device, and a coal powder storage device; and 8) starting a return water pump and transferring the treated excitation liquid to a water tank for recycling, wherein the monitoring and control simulation subsystem collects corresponding related data such as a time, pressure, a temperature, stress-strain, saturation, a voltage/current, sedimentation solid mass, produced liquid mass, and a produced gas flow while controlling the foregoing respective steps, and records the data as a data file.

2. The simulation test method for gas extraction from a tectonically-deformed coal seam in-situ by depressurizing a horizontal well cavity according to claim 1, wherein in step 3), three-stage reaming rates are respectively 150%, 200%, and 300%, and a diameter increase after reaming is 200% to 300%.

3. The simulation test method for gas extraction from a tectonically-deformed coal seam in-situ by depressurizing a horizontal well cavity according to claim 1, wherein in step 5), a depressurization excitation range after the pressure-pulse excitation and the stress release are performed on the horizontal well is ≥15.

4. The simulation test method for gas extraction from a tectonically-deformed coal seam in-situ by depressurizing a horizontal well cavity according to claim 3, wherein in step 6), coal powder concentration after pulverization is ≤50%.

5. The simulation test method for gas extraction from a tectonically-deformed coal seam in-situ by depressurizing a horizontal well cavity according to claim 3, wherein in step 5), the high-pressure high-speed fluids are mixed with a particular proportion of an abrasive.

* * * * *

UNITED STATES PATENT AND TRADEMARK OFFICE
CERTIFICATE OF CORRECTION

PATENT NO. : 10,995,572 B2
APPLICATION NO. : 16/761497
DATED : May 4, 2021
INVENTOR(S) : Shuxun Sang et al.

It is certified that error appears in the above-identified patent and that said Letters Patent is hereby corrected as shown below:

On the Title Page

Item (72), should read:
Shuxun Sang, Jiangsu (CN);
Xiaozhi Zhou, Jiangsu (CN);
Liwen Cao, Jiangsu (CN);
Shiqi Liu, Jiangsu (CN);
Haiwen Wang, Shandong (CN);
Huihu Liu, Anhui (CN);
Zicheng Li, Hubei (CN);
Jinlong Jia, Hubei (CN);
Huazhou Huang, Jiangsu (CN);
Changjiang Liu, Shandong (CN);
Hongjie Xu, Anhui (CN);
Ran Wang, Jiangsu (CN);
Shuyun Zhu, Jiangsu (CN)

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*